United States Patent [19]
Koppel

[11] 3,962,232
[45] June 8, 1976

[54] 7-METHOXYCEPHALOSPORINS

[75] Inventor: Gary A. Koppel, Indianapolis, Ind.

[73] Assignee: Eli Lilly and Company, Indianapolis, Ind.

[22] Filed: Nov. 5, 1973

[21] Appl. No.: 413,097

[52] U.S. Cl. .............................. 260/243 C; 424/246
[51] Int. Cl.² .................................... C07D 501/20
[58] Field of Search ................................. 260/243 C

[56] References Cited
UNITED STATES PATENTS

| | | | |
|---|---|---|---|
| 3,775,410 | 11/1973 | Christensen et al. | 260/243 C |
| 3,780,034 | 12/1973 | Christensen et al. | 260/243 C |
| 3,780,037 | 12/1973 | Hazen | 260/243 C |

FOREIGN PATENTS OR APPLICATIONS

| | | | |
|---|---|---|---|
| 71/3229 | 5/1971 | South Africa | 260/243 C |

*Primary Examiner*—Nicholas S. Rizzo
*Attorney, Agent, or Firm*—William C. Martens, Jr.; Everet F. Smith

[57] ABSTRACT

7β-acylamido-7α-methoxycephalosporin compounds in which the acylamido group has the formula

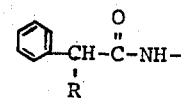

in which R is carboxy, protected carboxy, phosphono, protected phosphono, sulfo, or protected sulfo. The compounds exhibit antibiotic activity, in particular against Pseudomonas and Serratia type microorganisms.

5 Claims, No Drawings

7-METHOXYCEPHALOSPORINS

BACKGROUND OF THE INVENTION

This invention relates to certain 7-methoxylated 7-acylamidocephalosporins. In particular, this invention relates to certain of such cephalosporins having in the 7-position an α-carboxyphenylacetamido group, a protected α-carboxyphenylacetamido group, an α-sulfophenylacetamido group, a protected α-sulfophenylacetamido group, an α-phosphonophenylacetamido group, or a protected α-phosphonophenylacetamido group. The compounds of this invention have been found to exhibit particular activity against Pseudomonas and Serratia type microorganisms, which microorganisms customarily are, at best, only moderately susceptible to treatment by cephalosporin antibiotics.

Cephalosporin antibiotics having a methoxyl group at the 7-position are known. For example, 7-methoxycephalosporin C and 7-(5-amino-5-carboxyvaleramido)-7-methoxy-3-carbamoyloxymethyl-3-cephem-4-carboxylic acid have been obtained by the fermentation of *Streptomyces lipmanii* and *Streptomyces clavuligerus* as described in *J. Am. Chem. Soc.* 93, 2308 (1971).

Additionally, a number of 7-acylamido-7-methoxycephalosporin antibiotics have been prepared by the direct methoxylation procedure described in co-pending application Ser. No. 301,694 filed Oct. 27, 1972, now abandoned and a continuation-in-part of application Ser. No. 222,293 filed Jan. 31, 1972, and now abandoned. According to this method, a 7-acylamidocephalosporin is reacted at about −80°C. with lithium methoxide in methanol, and the product therefrom is reacted with a positive halogen compound such as t-butyl hypochlorite to provide a 7-acylamido-7-methoxycephalosporin.

7-Amino-7-methoxycephalosporanic acid has been prepared by cleavage of 7-methoxycephalosporin C via the phosphorus pentachloride/pyridine/methanol procedure as described in co-pending application Ser. No. 139,914 filed May 3, 1971, and now abandoned.

7-Amino-7-methoxycephalosporin esters can also be prepared by a process which is the subject of co-pending application Ser. No. 381,470 filed July 23, 1973 now U.S. Pat. No. 3,897,424. This process includes the steps of low temperature 7-methoxylation of a 7-(p-nitrobenzyloxycarbamido)cephalosporin ester; reduction of the methoxylation product to an intermediate reduction product; and treatment of the intermediate reduction product with silica gel.

The compounds of this invention are prepared by conventional acylation of the aforedescribed 7-amino-7-methoxycephalosporin esters employing a suitable acylating agent having the reactive α-substituent appropriately protected. The resulting product may or may not thereafter be cleaved in accordance with recognized techniques in order thereby to produce the corresponding free acid cephalosporin.

SUMMARY OF THE INVENTION

The compounds of this invention have the formula

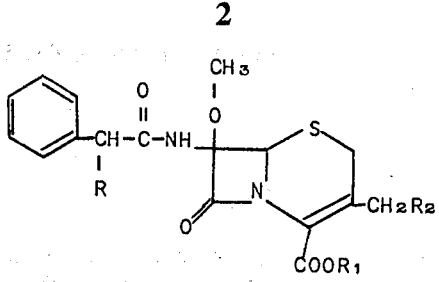

in which R is carboxy, protected carboxy, sulfo, protected sulfo, phosphono, or protected phosphono;

$R_1$ is hydrogen, an alkali metal cation, or aa readily removable ester forming group; and $R_2$ is $C_2$–$C_4$ alkanoyloxy, pyridinium,

in which Y is O or S, and $R_3$ is hydrogen, $C_1$–$C_4$ alkyl, or phenyl; or $R_2$ is a carbamoyloxy group of the formula

in which $R_4$ and $R_5$ are the same or different and are hydrogen or $C_1$–$C_4$ alkyl.

DETAILED DESCRIPTION OF THE INVENTION

As hereinbefore indicated, the compounds of this invention have the formula

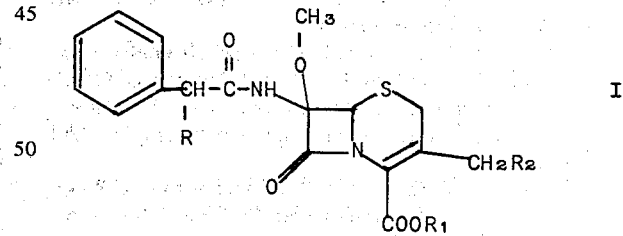

I

R in Formula I is carboxy, protected carboxy, sulfo, protected sulfo, phosphono, or protected phosphono.

The term "protected" when used in reference to "protected carboxy" refers to typical acid protecting groups, and generally to ester-forming groups. Preferably, although not essentially, the protecting group will be a readily cleavable ester moiety, such as, for example, $C_4$–$C_6$ tert-alkyl, $C_5$–$C_6$ tert-alkenyl, $C_5$–$C_6$ tert-alkynyl, benzyl, diphenylmethyl, p-nitrobenzyl, p-methoxybenzyl, 2,2,2trichloroethyl, phenacyl, trimethylsilyl, and the like.

Preferred groups for protection of the carboxy function are t-butyl, benzyl, and benzhydryl.

The unprotected phosphono group has the structure

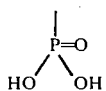

The term "protected phosphono" refers to displacement of each hydrogen by an ester-forming group. Typical such groups include, for example, lower alkyl, such as methyl, ethyl, isopropyl, t-butyl, and the like; aryl, such as phenyl, tolyl, ethylphenyl, and the like; and aralkyl, such as benzyl, and the like; as well as any of those mentioned hereinabove with respect to "protected carboxy" functions. Several of such groups are further delineated in German Patent Nos. 2,208,272 and 2,208,273.

The unprotected sulfo group has the formula $-SO_3H$. The term "protected sulfo" refers to displacement of the hydrogen by an ester-forming group, typically any of those mentioned hereinabove with respect to the protected carboxy or protected phosphono substituents.

When R is unprotected carboxy, phosphono, or sulfo, it is intended herein that it include not only the acid form thereof but also the salt form, specifically an alkali metal salt, such as lithium, sodium or potassium. In the case of the phosphono substituent, of course, the salt derivative can be either in the mono- or the di-basic form.

Preferably, R is carboxy, its alkali metal salt, or protected carboxy.

$R_1$ of Formula I is hydrogen, an alkali metal cation, such as lithium, sodium, or potassium, or a readily removable ester forming group. The term "a readily removable ester forming group" refers to the commonly employed carboxylic acid protecting groups used to block the $C_4$ carboxylic acid group of the cephalosporin molecule. Such groups are readily removable by conventional techniques and include, for example, $C_4-C_6$ tert-alkyl, $C_5-C_6$ tert-alkenyl, $C_5-C_6$ tert-alkynyl, benzyl, diphenylmethyl, p-nitrobenzyl, p-methoxybenzyl, 2,2,2-trichloroethyl, phenacyl, trimethylsilyl, and other like cleavable moieties.

Examples of $C_4-C_6$ tert-alkyl groups include, for example, t-butyl, t-amyl, and t-hexyl. Examples of $C_5-C_6$ tert-alkenyl groups are t-pentenyl and t-hexenyl. Examples of $C_5-C_6$ tert-alkynyl groups are t-pentynyl and t-hexynyl.

When $R_1$ is a readily removable ester forming group, preferably it is t-butyl, diphenylmethyl, benzyl, p-nitrobenzyl, or trimethylsilyl.

Most preferably, $R_1$ is hydrogen or an alkali metal cation. These $R_1$ substituents define those compounds of this invention which are most active antibiotically.

Cleavage of the ester moiety to the free 4-carboxyl function is desirable to produce an antibiotically active cephalosporin and is achieved by conventional treatment. This includes, for example, treatment of the ester with an acid such as trifluoroacetic acid, hydrochloric acid, and the like, or with zinc and acid, such as formic acid, acetic acid, hydrochloric acid, and the like. Cleavage likewise can be accomplished by hydrogenating the ester in the presence of palladium, rhodium, or a compound thereof, in suspension or on a carrier such as barium sulfate, carbon, alumina, or the like. These cleavage techniques likewise can be employed to remove the protecting group which may be present on the carboxy, phosphono, or sulfo group which is located in the α-position of the 7-phenylacetamido substituent of the compounds of this invention.

$R_2$ of Formula I is $C_2-C_4$ alkanoyloxy, pyridinium,

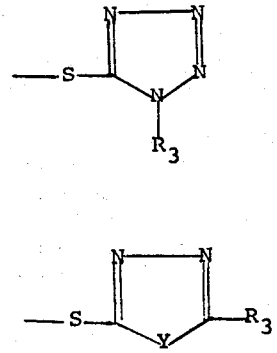

in which Y is O or S, and $R_3$ is hydrogen, $C_1-C_4$ alkyl, or phenyl; or $R_2$ is a carbamoyloxy group of the formula

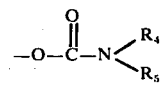

in which $R_4$ and $R_5$ are the same or different and are hydrogen or $C_1-C_4$ alkyl.

The term "$C_2-C_4$ alkanoyloxy" includes, for example, acetoxy, propionoxy, butanoyloxy, and the like.

Illustrative of the instance in which $R_2$ in Formula I is

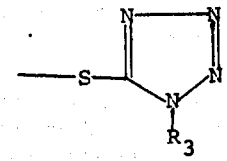

are the following: 1H-tetrazol-5-ylthiol, 1-methyl-1H-tetrazol-5-ylthio, 1-n-butyl-1H-tetrazol-5-ylthio, 1-phenyl-1H-tetrazol-5-ylthio, 1-ethyl-1H-tetrazol-5-ylthio, 1-n-propyl-1H-tetrazol-5-ylthio, 1-isopropyl-1H-tetrazol-5-ylthio, 1-isobutyl-1H-tetrazol-5-ylthio, 1-sec-butyl-1H-tetrazol-5-ylthio, 1-t-butyl-1H-tetrazol-5-ylthio, and the like.

Illustrative of the instance in which $R_2$ in Formula I is

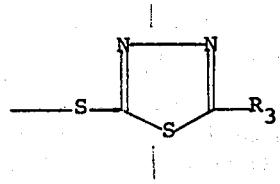

are the following: 1,3,4-thiadiazol-2-ylthio, 5-methyl-1,3,4-thiadiazol-2-ylthio, 5-n-butyl-1,3,4-thiadiazol-2-ylthio, 5-phenyl-1,3,4-thiadiazol-2-ylthio, 5-ethyl-1,3,4-thiadiazol-2-ylthio, 5-n-propyl-1,3,4-thiadiazol-2-ylthio, 5-isopropyl-1,3,4-thiadiazol-2-ylthio, 5-isobutyl-1,3,4-thiadiazol-2-ylthio, 5-sec-butyl-1,3,4-thiadiazol-2-ylthio, 5-t-butyl-1,3,4-thiadiazol-2-ylthio, and the like.

Illustrative of the instance in which $R_2$ in Formula I is

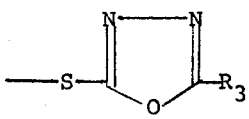

are the following: 1,3,4-oxadiazol-2-ylthio, 5-methyl-1,3,4-oxadiazol-2-ylthio, 5-n-butyl-1,3,4-oxadiazol-2-ylthio, 5-phenyl-1,3,4-oxadiazol-2-ylthio, 5-ethyl-1,3,4-oxadiazol-2-ylthio, 5-n-propyl-1,3,4-oxadiazol-2-ylthio, 5-isopropyl-1,3,4-oxadiazol-2-ylthio, 5-isobutyl-1,3,4-oxadiazol-2-ylthio, 5-sec-butyl-1,3,4-oxadiazol-2-ylthio, 5-t-butyl-1,3,4-oxadiazol-2-ylthio, and the like.

Illustrative of the instance in which $R_2$ in Formula I is

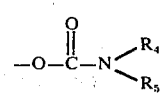

are the following: carbamoyloxy, N-methylcarbamoyloxy, N,N-dimethylcarbamoyloxy, N-ethylcarbamoyloxy, N,N-diethylcarbamoyloxy, N-butylcarbamoyloxy, N-methyl-N-ethycarbamoyloxy, N-methyl-N-butylcarbamoyloxy, N-ethyl-N-propyl-carbamoyloxy, N-propylcarbamoyloxy, N,N-dibutylcarbamoyloxy, and the like.

Preferably, $R_2$ is acetoxy, carbamoyloxy, 1-methyl-1H-tetrazol-5-ylthio, or 5-methyl-1,3,4-thiadiazol-2-ylthio.

The following compounds are illustrative of the 7-methoxy 7-acylamidocephalosporin compounds provided by the present invention. Each of the following compounds is described in the form of its free acid. It should be noted that each of these compounds can exist in the form of its alkali metal salt or in the form of an ester containing a readily removable ester forming group. Each of the compounds in any of these forms constitutes a part of this invention.

7β-(α-carboxy)phenylacetamido-7α-methoxy-3-acetoxymethyl-3-cephem-4-carboxylic acid;

7β-(α phosphono)phenylacetamido-7α-methoxy-3-propanoyloxymethyl-3-cephem-4-carboxylic acid;

7β-(α-sulfo)phenylacetamido-7α-methoxy-3-butanoyloxymethyl-3-cephem-4-carboxylic acid;

7β-(α-t-butoxycarbonyl)phenylacetamido-7α-methoxy-3-pyridinomethyl-3-cephem-4-carboxylic acid;

7β-(α-dimethylphosphono)phenylacetamido-7α-methoxy-3-(1H-tetrazol-5-ylthiomethyl)-3-cephem-4-carboxylic acid;

7β-(α-methylsulfo)phenylacetamido-7α-methoxy-3-(1-methyl-1H-tetrazol-5-ylthiomethyl)-3-cephem-4-carboxylic acid;

7β-(α-benzhydryloxycarbonyl)phenylacetamido-7α-methoxy-3-(1-phenyl-1H-tetrazol-5-ylthiomethyl)-3-cephem-4-carboxylic acid;

7β-(α-diphenylphosphono)phenylacetamido-7α-methoxy-3-(1,3,4-thiadiazol-2-ylthiomethyl)-3-cephem-4-carboxylic acid;

7β-(α-phenylsulfo)phenylacetamido-7α-methoxy-3-(5-methyl-1,3,4-thiadiazol-2-ylthiomethyl)-3-cephem-4-carboxylic acid;

7β-(α-p-nitrobenzyloxycarbonyl)phenylacetamido-7α-methoxy-3-(5-n-butyl-1,3,4-thiadiazol-2-ylthiomethyl)-3-cephem-4-carboxylic acid;

7β-(α-diethylphosphono)phenylacetamido-7α-methoxy-3-(1,3,4-oxadiazol-2-ylthiomethyl)-3-cephem-4-carboxylic acid;

7β-(α-benzylsulfo)phenylacetamido-7α-methoxy-3-(5-methyl-1,3,4-oxadiazol-2-ylthiomethyl)-3-cephem-4-carboxylic acid;

7β-(α-benzyloxycarbonyl)phenylacetamido-7α-methoxy-3-(5-phenyl-1,3,4-oxadiazol-2-ylthiomethyl)-3-cephem-4-carboxylic acid;

7β-(α-phosphono)phenylacetamido-7α-methoxy-3-carbamoyloxymethyl-3-cephem-4-carboxylic acid;

7β-(α-sulfo)phenylacetamido-7α-methoxy-3-(N,N-dimethylcarbamoyloxymethyl)-3-cephem-4-carboxylic acid;

7β-(α-carboxy)phenylacetamido-7α-methoxy-3-(N,N-diethylcarbamoyloxymethyl)-3-cephem-4-carboxylic acid; and the like.

Preferred compounds of this invention include those in which R is carboxy, $R_1$ is hydrogen, and $R_2$ is acetoxy, carbamoyloxy, or 1-methyl-1H-tetrazol-5-ylthio, as well as alkali metal disalts of such compounds.

As indicated hereinbefore, the compounds of this invention can be prepared by acylating a 7-amino-7-methoxy cephalosporin ester.

One method, specifically referred to hereinbefore, involves the following overall sequence:

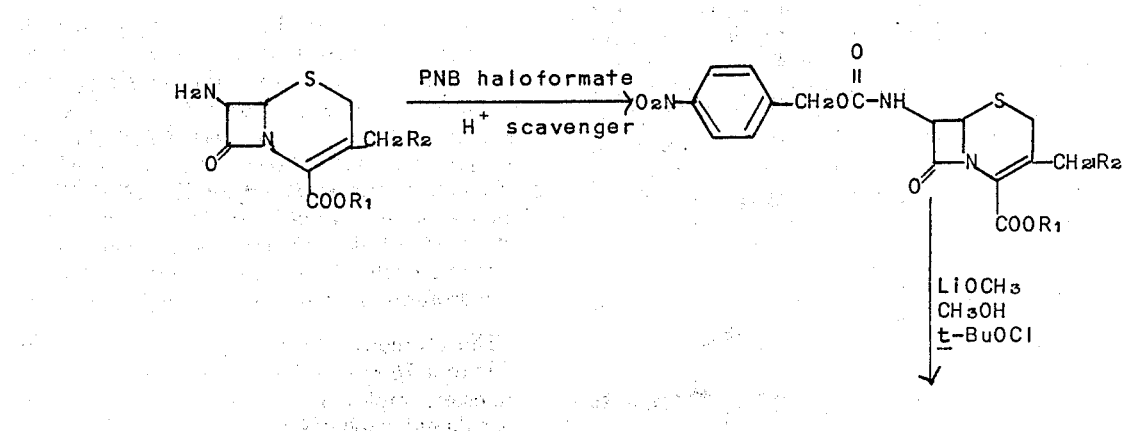

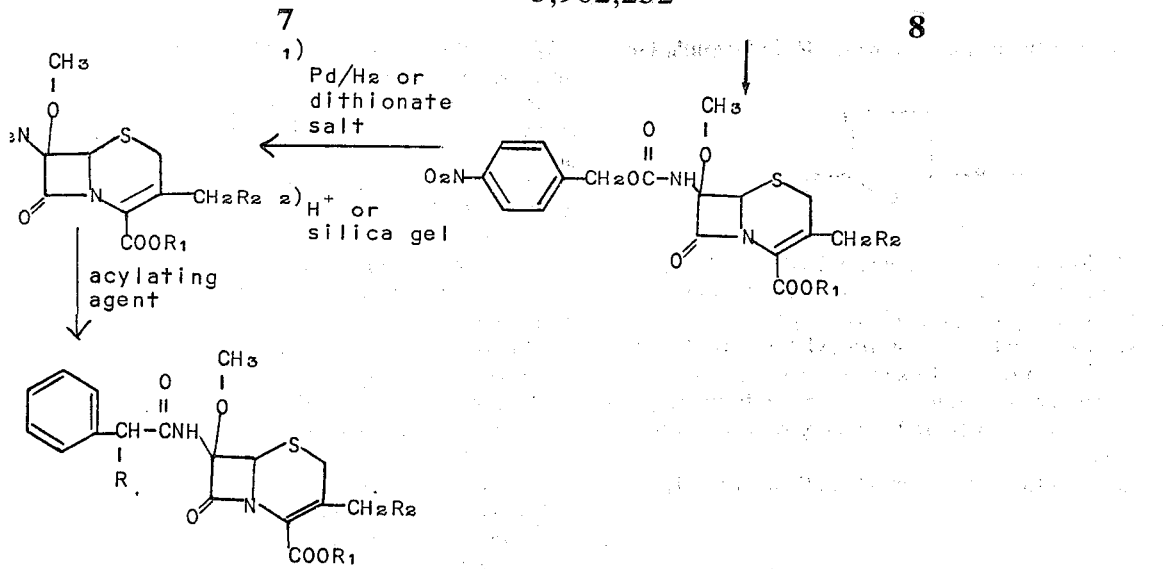

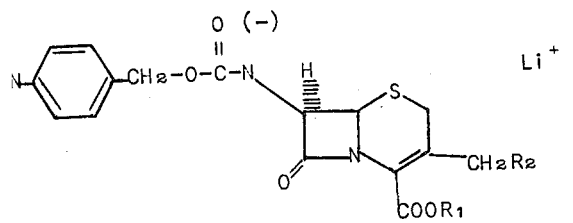

In the first step for production of the compounds of [th]is invention, a 7-aminocephalosporin ester is con[ve]rted to its corresponding 7β-(p-nitrobenzyloxycar- bamido)cephalosporin ester. This is accomplished by [ac]ylating the 7-amino compound with a haloformate [es]ter of p-nitrobenzyl alcohol.

This acylation is carried out in an inert solvent in the [pr]esence of an acid scavenging reagent, for example, a [ter]tiary amine such as triethylamine, N,N-diethylani[lin]e, pyridine, or an inorganic base such as sodium or [po]tassium bicarbonate or carbonate. Inert solvents [wh]ich can be employed in the acylation reaction in[cl]ude, for example, acetone, ethyl acetate, acetonitrile, N-dimethylformamide, or any other suitable solubi[liz]ing agent. The haloformate esters of p-nitrobenzyl [alc]ohol which can be employed are the bromoformate [an]d the chloroformate esters. Preferably, the chloro[for]mate ester is employed.

[I]t is also possible to employ the 7-aminocephalospo[rin] in the form of its free acid, and the resulting 7β-(p-[nit]robenzyloxycarbamido)cephalosporin can then be [est]erified. Under this latter acylation procedure, the [fre]e acid form of the cephalosporin preferably is solubi[liz]ed in the inert solvent prior to acylation by forming a [sol]uble bis-trimethylsilyl derivative thereof. Thus, for [ex]ample, a suspension of the free acid cephalosporin in [the] solvent is treated with an excess of N,O-bis-trime[thy]lsilylacetamide to form the soluble silyl derivative. [Th]e trimethylsilyl derivative is then acylated with the [p-n]itrobenzyl haloformate to provide, after hydrolysis, [the] corresponding 7β-(p-nitrobenzyloxycarbamido)-[cep]halosporin in the form of its free acid.

[T]he next step in producing the compounds of this [inv]ention involves reacting the 7β-(p-nitrobenzylox[yca]rbamido) cephalosporin ester in an inert, anhydrous [sol]vent at a temperature between about −120°C. and [−]5°C., and preferably between about −100°C. and [−]5°C., with from about 2 to about 6 molar equivalents [of l]ithium methoxide in excess methanol to generate, in [sit]u, the anionic form of the starting material repre[sen]ted by the formula

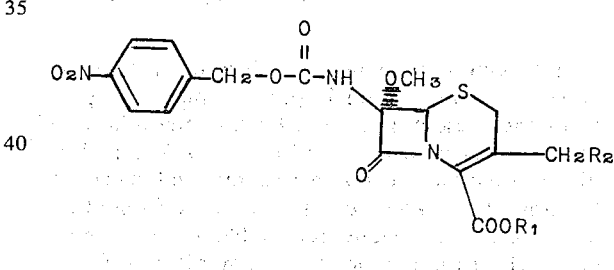

The above anionic form is generated rapidly and is substantially stable at the reaction temperature. The resulting reaction mixture is stirred for about 5 minutes to ensure completion of generation of the anionic form. At least one molar equivalent of t-butyl hypochlorite is then added to the cold, stirred reaction mixture. Stirring is continued for an additional 15 to 20 minutes, and the mixture is then acidified, preferably with formic acid or a lower alkyl carboxylic acid such as glacial acetic acid. This provides a 7-methoxylated derivative of the formula Upon completion of addition of the carboxylic acid, any excess t-butyl hypochlorite which may be present in the reaction mixture preferably is destroyed by adding trimethylphosphite to the cold acidified mixture in an amount corresponding to the excess of the t-butyl hypochlorite used in the reaction.

Inert solvents which can be employed include, for example, tetrahydrofuran, dioxane, the dimethyl ether of ethylene glycol, N,N-dimethylformamide, N,N-dimethylacetamide, and polyethers such as diethylene glycol dimethyl ether. Any suitable inert solvent which will provide a fluid reaction medium at the temperature of reaction may be employed. However, such solvents should be substantially anhydrous since water may interfere with the anion formation and thereby reduce the yield of the methoxylated product. Preferably, tetrahydrofuran is employed as solvent.

The aforedescribed methoxylation procedure, specific to a 7β-(p-nitrobenzyloxycarbamido)cephalosporin ester, employs procedures for the methoxylation of 7-acylamidocephalosporins described in co-pending application Ser. No. 301,694 filed Oct. 27, 1972.

When $R_2$ is a 1H-tetrazol-5-ylthio, a 1,3,4-thiadiazol-2-ylthio, or a 1,3,4-oxadiazol-2-ylthio group, the methoxylation reaction preferably is carried out at a temperature in the lower portion of the described reaction temperature range, for example, at a temperature between about −120°C. and −70°C.

The next step in preparing the compounds of this invention involves cleavage of the p-nitrobenzyloxycarbonyl group from the prepared 7β-(p-nitrobenzyloxycarbamido)-7α-methoxycephalosporin ester. The p-nitrobenzyloxycarbonyl group can be cleaved to obtain the 7-methoxylated cephalosporin ester by a two-step procedure which includes, first, the mild reduction of the 7β-(p-nitrobenzyloxycarbamido) group to obtain an intermediate reduction product, and, secondly, the treatment of the reduction product under mildly acidic conditions to effect removal of the reduced side chain.

The first step of this two-step cleavage, that is, the reduction step, is carried out by hydrogenation in the presence of a palladium catalyst or by means of an alkali or alkaline earth metal dithionate in buffered solution.

In the event that the first step of the two-step cleavage reaction involves reduction by hydrogenation, the 7β-(p-nitrobenzyloxycarbamido)-7α-methoxycephalosporin ester preferably is dissolved in an inert solvent and hydrogenated in the presence of a palladium catalyst until hydrogen absorption ceases. The hydrogenation is carried out generally between about 20°C. and 35°C., preferably at about room temperature, and under a hydrogen pressure of from about 1 to about 5 atmospheres. Reduction proceeds slowly with hydrogen uptake continuing over a period of about 12 hours. The rate of hydrogenation can be enhanced by the addition of a small amount of pyridine to the hydrogenation mixture.

The reduction continues until approximately 3 moles of hydrogen per mole of the substrate compound have been absorbed. The reduction mixture then is filtered to remove the catalyst, and the filtrate is evaporated in vacuo to dryness to yield the reduction product as a residue.

The hydrogenation can be carried out in a suitable inert non-reducible solvent inert non-reducible solvent such as tetrahydrofuran, dioxane, or N,N-dimethylformamide. Any such inert solvent in which the methoxylated intermediate is at least partially soluble can be employed. Preferably, tetrahydrofuran is employed since the starting materials are substantially soluble therein at room temperature.

Palladium catalysts which can be employed include finely divided palladium either alone or on an inert support such as carbon, alumina, kieselguhr, barium carbonate, silica, or any other inert support. A preferred catalyst form is one having from 5% to 10% palladium on carbon. For best results the catalyst is prereduced, and for each gram of substrate which is to be reduced, generally between 0.5 and 1 g. of catalyst is employed.

Another method of achieving reduction by the first of the two-step cleavage procedure involves the use of an alkali or an alkaline earth metal salt of a dithionic acid ($H_2S_2O_6$) in an inert, water miscible solvent which has been buffered to maintain the pH of the mixture at about pH 7 to pH 8. Typical dithionate salts include potassium dithionate, sodium dithionate, calcium dithionate, and the like; however, sodium dithionate is preferred.

The reduction using a dithionate salt is carried out at a temperature of from about −5°C. to about 25°C., and, preferably, 0°C. to 10°C. Water miscible inert solvents which can be employed include, for example, methanol, ethanol, isopropanol, acetonitrile, N,N-dimethylformamide, and the like. Mixtures of water miscible inert solvents can also be used, and, for example, a mixture of methanol and acetonitrile is a preferred such mixture.

The reduction mixture is buffered to maintain a pH at about pH 7 to pH 8. Dibasic phosphate buffer ($K_2HPO_4$) is a convenient buffer since it maintains the pH of the mixture at about pH 7.0–7.5.

The dithionate salt generally is employed in substantial excess, for example, approximately 10 moles of the dithionate salt per mole of the cephalosporin ester can be employed.

The reduction using a dithionate salt generally is carried out by adding a buffered solution of the dithionate salt, preferably sodium dithionate, to a cold (0°C. to 15°C.) solution of the cephalosporin ester with stirring. The addition preferably is carried out portionwise or dropwise, although this is not critical. Generally, the reduction is essentially complete upon completion of addition of the dithionate salt.

Following the addition of the buffered dithionate salt solution, the resulting reaction mixture is poured into a mixture of a water immiscible organic solvent and dibasic phosphate buffer. Suitable such organic solvents include, for example, ethyl acetate, methylene chloride, chloroform, and the like. The resulting intermediate reduction product is then extracted into the organic solvent, and the solution is washed, dried, and evaporated to yield the intermediate reduction product.

In those instances in which the group $R_2$ of the cephalosporin ester which is being reduced is a 1H-tetrazol-5-ylthio, a 1,3,4-thiadiazol-2-ylthio, or a 1,3,4-oxadiazol-2-ylthio, the reduction step preferably is carried out using a buffered dithionate salt. Although the hydrogenation technique can be employed, better yields of the reduction product, and, ultimately, of the final product are obtained using the buffered dithionate salt.

The second step of the two-step cleavage portion of the process for producing the compounds of this invention involves hydrolysis of the reduction intermediate under mildly acidic conditions.

The mildly acidic cleavage can be carried out in solution or in the presence of silica gel (silicic acid in gel form). Accordingly, the intermediate reduction product is dissolved in an organic solvent such as, for example, ethyl acetate, acetonitrile, methylene chloride, and the like, and the resulting mixture is vigorously stirred or shaken with a dilute aqueous mineral acid such as, for example, hydrochloric acid, sulphuric acid, phosphoric acid, or the like, and the pH of the mixture is maintained between about pH 4 and pH 6. The resulting 7β-amino-7α-methoxycephalosporin ester is recovered from the organic phase in a conventional manner.

Preferably, however, the mildly acidic cleavage of the intermediate reduction product is carried out in the presence of silica gel. According to this preferred mode of cleavage, the intermediate reduction product is dissolved in a suitable solvent, for example, a chlorinated hydrocarbon, such as chloroform, methylene chloride, or the like; an ester, such as ethyl acetate, or the like; a ketone, such as acetone, methyl isobutyl ketone, or the like; an ether, such as tetrahydrofuran, dioxane, or the like; or any other suitable solvent. The silica gel then is added to the resulting solution. The solution is stirred for about two hours and is filtered. The silica gel then is washed on the filter, and the filtrate and washings are combined and evaporated in vacuo to dryness to yield the desired 7β-amino-7α-methoxycephalosporin ester.

In an alternative procedure, the reduction product can be passed over a column packed with silica gel at a rate controlled such that the intermediate reduction product will be cleaved on the gel to obtain the desired cleaved product.

The next step in carrying out the synthesis of the compounds of this invention involves the acylation of the 7β-amino-7α-methoxycephalosporin ester obtained by the previous reaction. Acylation of the 7β-amino substituent can be readily accomplished by conventional acylation procedures. Generally, these procedures involve use as acylating agent of an activated acid, such as an acid halide, an acid anhydride, or an activated ester. Acylation can also be accomplished using the acid itself when it is employed in conjunction with any of the commonly employed peptide coupling reagents. In any event, the particular acylating agent which is employed will have the moiety

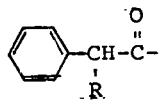

in which R is as hereinbefore defined. Thus, the compounds of this invention can be obtained by treating the 7β-amino-7α-methoxycephalosporin ester with an acid halide of the aforedescribed acyl moiety, particularly an acid chloride or an acid bromide. The acylation can be effected at a temperature of from about −50°C. to about +50°C., preferably from about −20°C. to about +30°C. The acylation can be effected in aqueous or non-aqueous media, suitable media including, for example, ketones or aqueous ketones, such as aqueous acetone and the like; halogenated hydrocarbons, for example, methylene chloride, chloroform, carbon tetrachloride, and the like; esters, such as ethyl acetate, and the like; amides, for example, N,N-dimethylformamide, N,N-dimethylacetamide, and the like; nitriles, for example, acetonitrile, and the like, or mixtures of any of the above.

The acid halide acylating agent can be prepared by reacting the corresponding acid or an alkali metal salt thereof, for example, the sodium or potassium salt, with a suitable halogenating agent, for example, phosphorus pentachloride, thionyl chloride, oxalyl chloride, and the like. Generally, acylation with an acid halide will be effected in the presence of an acid scavenging agent. Such agents include, for example, a tertiary amine, such as triethylamine, pyridine, quinoline, and the like; an inorganic base, such as, sodium bicarbonate, or the like; or an oxirane, such as a lower 1,2-alkylene oxide, for example, propylene oxide. The acid scavenging agent binds the hydrogen halide which is liberated as by-product during the acylation reaction.

The acylation can also be effected by employing the free acid form of the acylating agent in the presence of a suitable condensing agent. Condensing agents which can be employed in carrying out the acylation include carbodiimides, for example, N,N'-diethylcarbodiimide, N,N'-dipropylcarbodiimide, N,N'-diisopropylcarbodiimide, N,N'-dicyclohexylcarbodiimide, N-ethyl-N'-γ-dimethylaminopropylcarbodiimide, and the like; a suitable carbonyl compound, such as, carbonyldiimidazole, and the like; an isoxazolinium salt, such as N-ethyl-5-phenylisoxazolinium-3'-sulfonate, N-t-butyl-5-methylisoxazolinium perchlorate, and the like; as well as other recognized condensing agents. The acylation using this condensation reaction medium is effected under substantially anhydrous reaction conditions, and employs generally, for example, methylene chloride, N,N-dimethylformamide, acetonitrile, or such like solvent.

Another method for accomplishing acylation of the 7β-amino-7α-methoxycephalosporin ester involves employment of a symmetrical anhydride or a mixed anhydride of the acid corresponding to the acyl moiety. A typical mixed anhydride is that formed from pivalic acid and the acid containing the intended acyl moiety. Another typical mixed anhydride is that resulting from the reaction of the free acid containing the acyl moiety and a lower alkyl haloformate, for example, isobutyl chloroformate.

Another convenient method for achieving acylation of the 7β-amino-7α-methoxycephalosporin ester involves reaction thereof with an activated ester of the acid containing the acyl moiety. Typical such activated esters include the pentachlorophenyl ester, the p-nitrophenyl ester, and the 2,4-dinitrophenyl ester.

The compounds produced by the previously described acylation step are compounds of this invention. Typically, however, the compounds so resulting will be cephalosporin esters, and thus, most often, intermediates to the antibiotically active cephalosporin compounds.

The antibiotically active cephalosporin compounds generally will be obtained by cleavage of the ester function from the 4-carboxyl group. Generally, such conditions of cleavage will also accomplish the removal of any protecting group which may be present on the R substituent in the 7-acyl moiety. Cleavage of the ester moiety involves conventional methods well recognized in the art, and such methods have been predescribed hereinbefore. They include, for example, treatment of the ester as well as the protecting group present in the R substituent in the 7-acyl moiety with an acid such as trifluoroacetic acid, hydrochloric acid, or the like, or with zinc and acid, such as formic acid, acetic acid, hydrochloric acid, and the like. Hydrogenation techniques can also be employed by treatment of the ester intermediate in the presence of hydrogen and a catalyst such as palladium, rhodium, or a compound thereof, either in suspension or on a carrier such as barium sulfate, carbon, alumina, or the like.

The resulting cleaved compound can be recovered by conventional methods either in the form of its free acid or as an alkali metal salt thereof. Typically, the salt will be the sodium, potassium, or lithium salt, and, preferably, the sodium salt.

The compounds of this invention exhibit surprising activity against two difficultly controllable groups of microorganisms, specifically *Pseudomonas aeruginosa* and *Serratia morcescens*. This is especially surprising in view of the relative inactivity of the corresponding non-methoxylated cephalosporins against the same organisms. The data provided hereinbelow are minimum inhibitory concentrations (MIC) in micrograms of compound per milliliter of agar medium in standard gradient plate in vitro tests. The gradient plate procedure essentially is that described by Bryson and Szybalski, *Science*, 116, (1952), pp. 45–46. The inoculum treatment method was reported by Godzeski et al., *Antimicrobial Agents and Chemotherapy* (May, 1961) pp. 547–554.

The minimum inhibitory concentrations of certain of the compounds of this invention for *Pseudomonas aeruginosa* (X528) and *Serratia marcescens* (X99) are as follows:

7β-(α-carboxy)phenylacetamido-7α-methoxy-3-acetoxymethyl-3-cephem-4-carboxylic acid:
  X528/63.0; X99/3.1; the corresponding nonmethoxylated compound: X528/>200; X99/11.9.

7β-(α-carboxy)phenylacetamido-7α-methoxy-3-carbamoyloxymethyl-3-cephem-4-carboxylic acid:
  X528/118.0; X99/3.4; the corresponding nonmethoxylated compound: X528/>200; X99/17.0.

7β-(α-carboxy)phenylacetamido-7α-methoxy-3-(1-methyl-1H-tetrazol-5-ylthiomethyl)-3-cephem-4-carboxylic acid:
  X528/70; X99/0.3; the corresponding nonmethoxylated compound: X528/>200; X99/1.0.

The following examples are provided to further illustrate the compounds of this invention.

The abbreviations used in the examples refer to the following:

| | |
|---|---|
| THF | tetrahydrofuran |
| nmr | nuclear magnetic resonance spectrum |
| CDCl$_3$ | deuterated chloroform |
| D$_2$O | deuterated water |
| s | singlet |
| d | doublet |
| m | multiplet |

EXAMPLE 1

Diphenylmethyl 7β-(p-nitrobenzyloxycarboxamido)-7α-methoxycephalosporanate.

To a suspension of 64 g. of 7-aminocephalosporanic acid in 500 ml. of dry acetonitrile were added with stirring at room temperature 60 ml. of N,O-bis-trimethylsilylacetamide. A complete solution was obtained within 45 minutes with stirring. Approximately 90 minutes after the addition of the N,O-bis-trimethylsilylacetamide, 54.4 g. of p-nitrobenzyl chloroformate were added to the solution with stirring. After about one hour the reaction mixture was poured with vigorous agitation into two liters of ice water to precipitate the reaction product as an oily gum. Methylene chloride was added to the cold mixture to dissolve the gum. The two phase mixture was filtered through a filter aide to remove insolubles, and the organic phase of the clarified filtrate was separated. The organic phase was washed twice with water, and the product was extracted from the washed organic phase with an aqueous solution of sodium bicarbonate (52 g. in 500 ml. of water). The bicarbonate extract was washed twice with methylene chloride, diluted with 250 ml. of acetonitrile and one liter of ice water, and then acidified to pH 4.5 by the dropwise addition of 1N hydrochloric acid with vigorous stirring. The reaction mixture became viscous with the formation of a gelatinous precipitate and was diluted with three liters of water. With vigorous agitation the pH was lowered to pH 1.7 by the addition of 20% hydrochloric acid. The suspension was filtered, and the product was washed on the filter with water. The washed precipitate was dried in vacuo to give 66.7 g. of 7β-(p-nitrobenzyloxycarbamido)-cephalosporanic acid as an off-white powder.

To a solution of 61.5 g. of the dry reaction product in 200 ml. of dry tetrahydrofuran were added with stirring 32 g. of diphenyldiazomethane. Nitrogen evolution was essentially complete after 1 hour. After 2 hours the mixture was evaporated on a rotary evaporator to remove the solvent, and the oily residue was dissolved in a small volume of methylene chloride. The diphenylmethyl ester product was precipitated from solution as a heavy oil with hexane. The bulk of the methylene chloride was removed from the mixture by evaporation in vacuo, and the supernatant hexane was decanted from the oily residue. The oily product was purified by two successive precipitations from methylene chloride with hexane. The final light brown residue was dried in vacuo to give 85.3 g. of diphenylmethyl 7β-(p-nitrobenzyloxycarboxamido)cephalosporanate as a solid foam. Additional product was recovered from the pooled hexane supernatants.

To 150 ml. of dry tetrahydrofuran maintained under a nitrogen atmosphere at ice bath temperature were added with stirring 22 ml. of a solution of methyl lithium in ether followed by 35 ml. of methanol. After 10 minutes the mixture was cooled to a temperature of −70°C. in a dry ice acetone mixture, and a solution of 5.18 g. of diphenylmethyl 7β-(p-nitrobenzyloxycarboxamido)cephalosporanate in 50 ml. of dry tetrahydrofuran was added rapidly while the temperature was maintained below −65°C. After 5 minutes 1.26 ml. (10.6 mmole) of t-butyl hypochlorite were added rapidly to the reaction mixture. After about 40 minutes the reaction was quenched by adding 28 ml. of glacial acetic acid followed by 0.5 g. (0.47 ml.) of trimethylphosphite to destroy any excess oxidant. The reaction mixture was allowed to warm to 0°C. and was then evaporated in vacuo to a gum. The gummy residue was dissolved in methylene chloride, and the solution was washed with water, an aqueous solution of sodium bicarbonate, and then again with water. The washed solution was dried and evaporated to dryness to yield 4.57 g. of diphenylmethyl 7β-(p-nitrobenzyloxycarboxamido)-7α-methoxycephalosporanate as a solid foam.

EXAMPLE 2

Diphenylmethyl 7β-amino-7α-methoxycephalosporanate.

A suspension of 1.5 g. of 5% palladium on carbon in 25 ml. of tetrahydrofuran containing 0.661 ml. of pyridine was stirred for 30 minutes under a hydrogen pressure of two atmospheres. A solution of 4.32 g. of diphenylmethyl 7β-(p-nitrobenzyloxycarboxamido)-7α-methoxycephalosporanate in 50 ml. of tetrahydrofuran was added to the catalyst suspension, and the mixture was hydrogenated at room temperature for 6.5 hours under two atmospheres of hydrogen. The catalyst was filtered, and the filtrate was evaporated in vacuo to yield 4.10 g. of the reduction product.

The reduction product (1.5 g.) was dissolved in 24 ml. of methylene chloride, and 2.1 g. of silica gel (Merck 7729) were added. The suspension was stirred for 2 hours and was then filtered. The silica gel was washed on the filter with 36 ml. of methylene chloride, and the filtrate and washings were evaporated to yield 80 mg. of diphenylmethyl 7β-amino-7α-methoxycephalosporanate as a brown oil.

EXAMPLE 3

Diphenylmethyl
β-(α-t-butoxycarbonyl)phenylacetamido-7α-methoxycephalosporanate.

To 30 ml. of methylene chloride were added 354 mg. 1.5 millimoles) of t-butylphenylmalonic acid. To the resulting stirred solution maintained at ice bath temperature were added three drops of N,N-dimethylformamide and 0.25 ml. (3 millimoles) of oxalyl chloride. The resulting mixture was stirred at ice bath temperature for 1.5 hours. The solvent was then evaporated, the residue dissolved in benzene, and the benzene solution evaporated in vacuo.

To 20 ml. of methylene chloride were added 400 mg. diphenylmethyl 7β-amino-7α-methoxycephalosporanate. To the resulting mixture were then added 14 ml. (1.7 millimoles) of pyridine followed by the previously prepared t-butylpheylmalonyl chloride dissolved in 10 ml. of methylene chloride. The latter was added dropwise. The mixture was stirred at ice bath temperature for about 1 hour after addition of the acid chloride was complete. The reaction mixture was then evaporated to dryness and the residue was dissolved in ethyl acetate. The ethyl acetate solution was washed successively with 3 percent hydrochloric acid, saturated sodium bicarbonate solution, and saturated sodium chloride solution. The ethyl acetate layer was then dried over sodium sulfate and evaporated to afford 661 mg. of diphenylmethyl 7β-(α-t-butoxycarbonyl)phenylacetamido-7α-methoxycephalosporanate. nmr (CDCl$_3$): 4.93 (s, 1H, C$_6$H); 5.42 (s, 1H, H at C); 6.51 [2s(non-equivalent), 3H, C$_7$ methoxy] and (s, 3H, C$_3$ methyl); tau.

EXAMPLE 4

7β-(α-Carboxy)phenylacetamido-7α-methoxycephalosporanic acid, disodium salt.

To 0.5 ml. of a 50:50 mixture of trifluoroacetic acid and formic acid were added 40 mg. of 7β-(α-t-butoxycarbonyl)phenylacetamido-7α-methoxycephalosporanate. Upon completion of solution, the mixture was stirred and allowed to warm to room temperature over a 6 minute period. To the mixture was then added ml. of methylene chloride. The mixture was evaporated, and the residue was dissolved in a small amount of ethyl acetate. The ethyl acetate solution was extracted with aqueous sodium bicarbonate solution. The sodium bicarbonate solution was separated from the organic and was acidified to pH 2.5 by addition of dilute acid. The acidified aqueous mixture then was extracted with ethyl acetate. The ethyl acetate extract was dried over sodium sulfate and evaporated to obtain mg. of 7β-(α-carboxy)phenylacetamido-7α-methoxycephalosporanic acid, sodium salt.
nmr (D$_2$O): 4.87 (s, 1H, C$_6$ H); 6.40, 6.54 [2S (non-equivalent), 3H, C$_7$ methoxy] and 7.92 (s, 3H, C$_3$ methyl); tau.

EXAMPLE 5

Diphenylmethyl
7β-(p-nitrobenzyloxycarbamido)-7α-methoxy-3-(1-methyl-1H-tetrazol-5-ylthiomethyl)-3-cephem-4-carboxylate.

Diphenylmethyl 7-(p-nitrobenzyloxycarbamido)-3-(1-methyl-1H-tetrazol-5-ylthiomethyl)-3-cephem-4-carboxylate was prepared by reacting p-nitrobenzyl chloroformate with diphenylmethyl 7-amino-3-(1-methyl-1H-tetrazol-5-ylthiomethyl)-3-cephem-4-carboxylate according to the acylation procedure described by Example 1. The carbamido tetrazole cephem ester product was methoxylated as follows.

To 125 ml. of dry THF under nitrogen at 5°C. were added 9.6 ml. of 1.83 N methyl lithium in diethyl ether and 20 ml. of dry methanol. The solution was cooled to a temperature of −94°C. in a bath of methanol and isobutanol which was treated with liquid nitrogen and ethanol. To the cold solution was added a solution of 3.37 g. (5 mmole) of diphenylmethyl 7-(p-nitrobenzyloxycarbamido)-3-(1-methyl-1H-tetrazol-5-ylthiomethyl)-3-cephem-4-carboxylate in 30 ml. of THF. The cold mixture was stirred for 2 minutes, and 0.8 ml. of t-butyl hypochlorite was added. The reaction mixture was allowed to warm to −70°C. over 30 minutes with stirring. The mixture was maintained at −70°C. for 10 minutes, and 20 ml. of glacial acetic acid and 1 ml. of trimethylphosphite were then added.

The reaction mixture was worked up and the product recovered by following the procedures described by Example 1 to afford 3.6 g. of crude diphenylmethyl 7β-(p-nitrobenzyloxycarbamido)-7α-methoxy-3-(1-methyl-1H-tetrazol-5-ylthiomethyl)-3-cephem-4-carboxylate. The product was purified by preparative thin layer chromatography.
nmr (CDCl$_3$): 3.5 (s, 1H, C$_7$ amide); 4.97 (s, 1H, C$_6$ H); 5.63 (d, 2H, C$_3$ methylene); 6.19 (s, 3H, tetrazole 1-methyl) and 6.43 (s, 3H, C$_7$ methoxy); tau.

EXAMPLE 6

Diphenylmethyl
7β-amino-7α-methoxy-3-(1-methyl-1H-tetrazol-5-ylthiomethyl)-3-cephem-4-carboxylate.

The product obtained as described in Example 5 (1.05 g., 1.5 mmole) was dissolved in a mixture of 15 ml. of acetonitrile and 60 ml. of methanol. The solution was stirred and cooled to ice bath temperature, and two 4.5 ml. portions of a solution of 1.74 g. (10 mmole) of sodium dithionate (Na$_2$S$_2$O$_6$) in 10 ml. of dibasic phosphate buffer were added over a 10 minute period. The reaction mixture was then poured into 200 ml. of a mixture of 50 ml. of ethyl acetate and 150 ml. of dilute dibasic phosphate buffer. The organic layer was separated and dried over magnesium sulfate. The dried extract was evaporated to dryness to yield the reduction product as a residue.

The residue was dissolved in 30 ml. of methylene chloride, and 2 g. of silica gel were suspended in the solution. The suspension was stirred for 3 hours at room temperature and filtered. The silica gel was washed on the filter with methylene chloride, and the filtrate was evaporated to dryness to yield 310 mg. of diphenylmethyl 7β-amino-7α-methoxy-3-(1-methyl-1H-tetrazol-5-ylthiomethyl)-3-cephem-4-carboxylate.

nmr (CDCl$_3$): 5.17 (s, 1H, C$_6$ hydrogen); 5.62 (d, 2H, C$_3$ methylene); 6.19 (s, 3H, tetrazole 1-methyl group) and 6.46 (s, 3H, C$_7$ methoxy); tau.

EXAMPLE 7

Diphenylmethyl 7β-(α-t-butoxycarbonyl)phenylacetamido-7α-methoxy-3-(1-methyl-1H-tetrazol-5-ylthiomethyl)-3-cephem-4-carboxylate.

The product from Example 6 (310 mg.) was dissolved in 20 ml. of methylene chloride, and the resulting mixture was stirred at ice bath temperature. To the mixture was then added 0.08 ml. (1 millimole) of pyridine. t-Butylphenylmalonyl chloride (232 mg.), prepared as in Example 3, dissolved in 10 ml. of methylene chloride, was added dropwise to the mixture. The resulting mixture was stirred for 1 hour. The solvents were evaporated, and the residue was dissolved in a 90:10 mixture of ethyl acetate and ethanol. The solution was washed successively with 3 percent hydrochloric acid, saturated sodium bicarbonate, and saturated sodium chloride. The organic layer was then dried over sodium sulfate and evaporated to obtain 400 mg. of crude diphenylmethyl 7β-(α-t-butoxycarbonyl)-phenylacetamido-7α-methoxy-3-(1-methyl-1H-tetrazol-5-ylthiomethyl)-3-cephem-4-carboxylate. The product was purified by preparative thin layer chromatography.

nmr (CDCl$_3$): 4.97 (s, 1H, C$_6$ H); 5.42 (s, 1H, H at α C); 6.16 (s, 3H, tetrazole 1-methyl) and 6.54 [2s (non-equivalent), 3H, C$_7$ methoxy]; tau.

EXAMPLE 8

7β-(α-Carboxy)phenylacetamido-7α-methoxy-3-(1-methyl-1H-tetrazol-5-ylthiomethyl)-3-cephem-carboxylic acid.

A mixture of 101 mg. of diphenylmethyl 7β-(α-t-butoxycarbonyl)phenylacetamido-7α-methoxy-3-(1-methyl-1H-tetrazol-5-ylthiomethyl)-3-cephem-4-carboxylate in 400 ml. of 97 percent formic acid was stirred for 45 minutes. The mixture was evaporated to obtain 62 mg. of 7β-(α-carboxy)phenylacetamido-7α-methoxy-3-(1-methyl-1H-tetrazol-5-ylthiomethyl)-3-cephem-carboxylic acid.

nmr (acetone d$_6$): 4.91 (s, 1H, C$_6$ H); 6.10 (s, 3H, tetrazole 1-methyl); and 6.52 [2s (non-equivalent), 3H, C$_7$ methoxy]; tau.

EXAMPLE 9

Diphenylmethyl 7β-(p-nitrobenzyloxycarbamido)-7α-methoxy-3-carbmaoyloxymethyl-3-cephem-4-carboxylate.

To 250 ml. of dry THF under nitrogen were added 19 ml. of 1.85 N methyl lithium in diethyl ether with stirring. Next, 40 ml. of dry methanol were slowly added, and the solution was allowed to stir for 10 minutes before being cooled in a dry ice-acetone bath. A solution of 6.18 g. (10 mmole) of diphenylmethyl 7β-(p-nitrobenzyloxycarbamido)-3-carbamoyloxymethyl-3-cephem-4-carboxylate in 80 ml. of THF was added to the cold solution; the mixture was stirred for 2 minutes and 2 ml. of t-butyl hypochlorite were then added. The cold raection mixture was stirred for 20 minutes, and 40 ml. of glacial acetic acid containing 2 ml. of trimethyl phosphite were added. The mixture was allowed to warm to room temperature and was evaporated. The residue was dissolved in dichloromethane. The solution was washed successively with a saturated sodium chloride solution and a saturated sodium bicarbonate solution and then dried. The dried solution was evaporated in vacuo to yield 6.6 g. of reaction product mixture.

The reaction product mixture was dissolved in 100 ml. of benzene containing 4% ethyl acetate, and the solution was chromatographed over a column packed with 300 g. of silica (containing 15% water and added to the column as a slurry in benzene).

Elution was carried out with benzene containing increasing percentages of ethyl acetate as follows:

| Volume of Eluant (liters) | Percent Ethyl Acetate in Benzene (v:v) |
|---|---|
| 1 | 4 |
| 1 | 8 |
| 2 | 12 |
| 2 | 16 |
| 1 | 20 |

Multiple fractions of 250 ml. each were collected and aliquots thereof were evaporated and the residual product assayed by nmr. Fractions 19–26 were combined and evaporated to dryness to yield 2.1 g. of diphenylmethyl 7β-(p-nitrobenzyloxycarbamido)-7α-methoxy-3-carbamoyloxymethyl-3-cephem-4-carboxylate.

nmr (CDCl$_3$): 4.94 (s, 1H, C$_6$H); 6.24 (s, 3H, C$_7$ methoxy) and 6.34–6.66 (m, 2H, C$_2$ hydrogen); tau.

EXAMPLE 10

Diphenylmethyl 7β-amino-7α-methoxy-3-carbamoyloxymethyl-3-cephem-4-carboxylate.

The 2.1 g. of product obtained as described in Example 9 were dissolved in 100 ml. of a 1:1 (v:v) mixture of methanol-THF, and a prereduced suspension of 2.1 g. of 5% palladium on carbon in 100 ml. of 1:1 McOH-THF was added. The mixture stirred at room temperature for 3.5 hours under one atmosphere of hydrogen. After hydrogen uptake had ceased, the mixture was filtered, and the filtrate was evaporated to yield 1.94 g. of the reduction product intermediate.

The intermediate was dissolved in 60 ml. of dichloromethane, and 5 g. of silica gel (Merck Chromatography Grade) were added. The suspension was stirred for 2 hours at room temperature and then filtered, and the filtrate was evaporated to yield 810 mg. of diphenylmethyl 7β-amino-7α-methoxy-3-carbamoyloxymethyl-3-cephem-4-carboxylate.

nmr (CDCl$_3$): 4.13 (broad s, 2H, carbamoyl NH); 5.06 (s, 1H, C$_6$ H); 6.50 (s, 3H, C$_7$ methoxy) and 7.19 (broad s, 2H, H$_2$N—C—OCH$_3$); tau.

EXAMPLE 11

Diphenylmethyl 7β-(α-t-butoxycarbonyl)phenylacetamido-7α-methoxy-3-carbamoyloxymethyl-3-cephem-4-carboxylate.

A mixture of 235 mg. of the product from Example 10 in 10 ml. of methylene chloride was prepared. To the mixture were added 0.16 ml. (1 millimole) of pyridine followed immediately by 5 ml. of methylene chloride containing 236 mg. (1 millimole) of t-butylphenylmalonyl chloride prepared as in Example 3. The latter was added dropwise to the mixture maintained at ice bath temperature. Addition time was about 5 minutes, and the mixture was stirred for an additional 25 minutes. The reaction mixture was then worked up according to the procedure described in Example 3 to provide 300 mg. of crude diphenylmethyl 7β-(α-t-butoxycarbonyl)phenylacetamido-7α-methoxy-3-carbamoyloxymethyl-3-cephem-4-carboxylate. The crude product was purified by preparative thin layer chromatography using a mixture of benzene and ethyl acetate to obtain 150 mg. of purified product.

nmr (CDCl$_3$): 4.97 (s, 1H, C$_6$ H); 5.38 (s, 1H, H at t-C) and 6.53 [2s (non-equivalent), 3H, C$_7$ methoxy];

EXAMPLE 12

7β-(α-Carboxy)phenylacetamido-7α-methoxy-3-carbamoyloxymethyl-3-cephem-4-carboxylic acid, disodium salt.

A mixture of 20 mg. of the product from Example 11 in 0.5 ml. of a 50:50 mixture of trifluoroacetic acid and formic acid was prepared at freezer temperature. The mixture was allowed to stand and warm to room temperature over a 15 minute period. To the mixture was then added 10 ml. of methylene chloride. The mixture was evaporated, and the residue was dissolved in a small amount of ethyl acetate. The ethyl acetate solution was extracted with aqueous sodium bicarbonate solution. The sodium bicarbonate solution was separated from the organic and was acidified to pH 2.5 by addition of dilute acid. The acidified aqueous mixture then was extracted with ethyl acetate. The ethyl acetate extract was dried over sodium sulfate and evaporated to obtain 9.4 mg. of 7β-(α-carboxy)phenylacetamido-7α-methoxy-3-carbamoyloxymethyl-3-cephem-4-carboxylic acid, disodium salt.

nmr (D$_2$O): 4.86 [2s (non-equivalent), 1H, C$_6$ H) and 6.40, 6.48 [2s (non-equivalent), 3H, C$_7$ methoxy]; tau.

I claim:
1. A compound of the formula

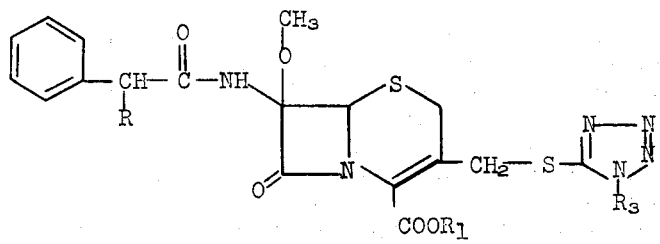

in which
R is carboxy or an alkali metal salt thereof;
R$_1$ is hydrogen, an alkali metal cation, or a readily removable ester forming group; and
R$_3$ is hydrogen, C$_1$–C$_4$ alkyl, or phenyl.
2. Compound of claim 1, in which R$_1$ is hydrogen, an alkali metal cation, or a readily removable ester forming group selected from the group consisting of C$_4$–C$_6$ tert-alkyl, C$_5$–C$_6$ tert-alkenyl, C$_5$–C$_6$ tert-alkynyl; benzyl, diphenylmethyl, p-nitrobenzyl, p-methoxybenzyl, 2,2,2-trichloroethyl, phenyl, and trimethylsilyl.
3. Compound of claim 2, in which R$_1$ is hydrogen or an alkali metal cation.
4. Compound of claim 2 in which R$_1$ is t-butyl, diphenylmethyl, benzyl, p-nitrobenzyl, or trimethylsilyl.
5. Compound of claim 1 in which R is carboxy, R$_1$ is hydrogen, and R$_2$ is 1-methyl-1H-tetrazol-5-ylthio, or a corresponding alkali metal disalt of said compound.

* * * * *